United States Patent
Reece et al.

(10) Patent No.: US 6,242,582 B1
(45) Date of Patent: Jun. 5, 2001

(54) METHOD OF DETECTION OF INFLUENZA VIRUS AND COMPOUNDS FOR USE THEREIN

(75) Inventors: Phillip A. Reece, Balwyn; Wen-Yang Wu; Betty Jin, both of Mt. Waverley; Guy Y. Krippner, Glen Waverley; Keith Geoffrey Watson, Surrey Hills, all of (AU)

(73) Assignee: Biota Scientific Management PTY Ltd., Melbourne (AU)

( * ) Notice: Subject to any disclaimer, the term of this patent is extended or adjusted under 35 U.S.C. 154(b) by 0 days.

(21) Appl. No.: 09/142,088

(22) PCT Filed: Feb. 26, 1997

(86) PCT No.: PCT/AU97/00109

§ 371 Date: Jan. 11, 1999

§ 102(e) Date: Jan. 11, 1999

(87) PCT Pub. No.: WO97/32214

PCT Pub. Date: Sep. 4, 1997

(30) Foreign Application Priority Data

Mar. 1, 1996 (AU) .................................. PN8397
Sep. 4, 1996 (AU) .................................. PO2131
Nov. 14, 1996 (AU) .................................. PO3631

(51) Int. Cl.$^7$ ............................ C07G 3/00; C07D 315/00
(52) U.S. Cl. ............................................ 536/4.1; 549/424
(58) Field of Search ............................ 549/424; 536/4.1; 436/93

(56) References Cited

U.S. PATENT DOCUMENTS

| | | | |
|---|---|---|---|
| 4,355,102 | 10/1982 | Quashi | ....................... 435/5 |
| 5,453,533 | * 9/1995 | Luo et al. | . |
| 5,919,819 | 7/1999 | Andrews et al. | ..................... 514/459 |

FOREIGN PATENT DOCUMENTS

| | | |
|---|---|---|
| 91/09971 | 7/1991 | (WO) . |
| 91/09972 | 7/1991 | (WO) . |
| 91/09975 | 7/1991 | (WO) . |
| 91/10744 | 7/1991 | (WO) . |
| 91/16320 | 10/1991 | (WO) . |
| 92/06691 | 4/1992 | (WO) . |
| 92/12256 | 7/1992 | (WO) . |

OTHER PUBLICATIONS

Spada et al.; "Comparison of Rapid Immunofluorescence Assay to Cell Culture Isolation for the Detection of Influenza A and B Viruses in Nasopharyngeal Secretions from Infants and Children"; Journal of Virological Methods; vol. 33; 1991; pp. 305–310.

Ryan–Poirier et al.; "Application of Directigen FLU–A for the Detection of Influenza A Virus in Human and Nonhuman Specimens"; Journal of Clinical Microbiology; vol. 30, No. 3; May 1992; pp. 1072–1075.

Leonardi et al.; "Comparison of Rapid Detection Methods for Influenza A Virus and Their Value in Health–Care Management of Institutionalized GeriatricPatients"; Journal of Clinical Microbiology; vol. 32, No. 1; Jan. 1994; pp. 70–74.

Waner et al.; "Comparison of Directigen FLU–A With Viral Isolation and Direct Immunofluorescence of the Rapid Detection and Identification of Influenza A Virus"; Journal of Clinical Microbiology; vol. 29, No. 3; Mar. 1991; pp. 479–482.

Von Iztstein et al.; "Rational Design of Potent Sialidase–based Inhibitors of Influenza Virus Replication"; Nature; vol. 363; Jun. 3, 1993; pp. 418–423.

Ryan et al.; "Inhibition of Influenza Virus Replication in Mice By GG167 (4–Guanidino-2,4–Dideoxy-2, 3–Dehydro–N–Acetylneuraminic Acid) is Consistent With Extracellular Activity of viral Neuraminidase (Sialidase)"; Antimicrobial Agents and Chemotherapy; vol. 38, No. 10; 2270–2275, Oct. 1994.

Hayden et al.; "Safety and Efficacy of the Neuraminidase Inhibitor GG167 in Experimental Human Influenza"; Journal of the American Medical Association; vol. 275, No. 4; Jan. 1996; pp. 295–299.

Kim et al.; "Influenza Neuraminidase Inhibitors Possessing a Novel Hydrophobic Interaction in the Enzyme—Active Site: Design, Synthesis and Structural Analysis of Carbocyclic Sialic Acid Analogues With Potent Anti–Influenza Activity"; J. Am. Chem. Soc.; vol. 119, No. 4; 1997; pp. 681–690.

* cited by examiner

Primary Examiner—Amelia Owens
(74) Attorney, Agent, or Firm—Foley & Lardner

(57) ABSTRACT

The invention provides a method of detection of influenza virus which utilizes compounds able to bind specifically to the active site of influenza virus neuraminidase, and novel compounds for use in the method.

18 Claims, No Drawings

METHOD OF DETECTION OF INFLUENZA VIRUS AND COMPOUNDS FOR USE THEREIN

This invention relates to diagnostic methods, and in particular to methods for diagnosis of influenza virus infection. The invention provides a novel diagnostic method which can be used for detection of all strains of influenza virus Type A and Type B. The method is based on the use of compounds able to bind specifically to the active site of influenza virus neuraminidase, or functionalised derivatives of such compounds, as binding and/or detecting agents to identify influenza virus in clinical specimens. The term "neuraminidase binders" is used hereinafter to refer to these compounds and their functionalized derivatives. The method and compounds of the invention can function either in the presence or the absence of compounds binding non-specifically to influenza virus neuraminidase.

The invention particularly relates to a new class of chemical compounds and their use as diagnostic agents for the visual or instrumental detection of influenza A and B. More specifically the invention concerns a group of novel neuraminic acid (sialic acid) derivatives which bind to influenza A and B neuraminidase, and which also have a functionality which allows the compounds to be bound to a surface or to a detectable label.

BACKGROUND OF THE INVENTION

Influenza A and B viruses are major causes of acute respiratory disease, with an estimated 30–50 million infections annually in the United States alone. Influenza A has been responsible for major epidemics, such as the "Spanish Flu" of 1919 which killed millions of people. Many viral and bacterial infections may present with symptoms similar to those of influenza. The rapid identification of respiratory viruses would enable physicians to use the most appropriate therapy early in the illness. For example, an early and accurate diagnosis would allow decisions regarding the use of antibacterial therapy and hospitalisation of children and the elderly.

Laboratory tests for the identification of viruses in clinical material are widely used, and a variety of different detection methodology is available. The textbook, "Laboratory Diagnosis of Viral Infections", Marcel Dekker 1992, Ed E. H. Lennette generally discusses methods which are used for a wide range of viruses, including influenza virus.

A nester of tests are available for the diagnosis of influenza A and B. The traditional method of identifying influenza viruses has been the use of cell culture, which is highly sensitive and specific. Unfortunately, the time required for culture, isolation and identification of influenza virus can range between 2 and 10 days, thus making it virtually useless in guiding the physician to an appropriate therapy. Since influenza virus infection is normally self-limited, diagnosis must be rapid if therapy is to be effective. In other words, such cell culture methods are normally only of value in providing retrospective epidemiological information.

In addition to the cell culture methods for detecting influenza, there have recently become available a few rapid direct tests, which are specific for influenza A. Thus, a monoclonal immunofluorescence assay (IFA) has been reported (Spada, B. et al, J. Virol. Methods, 1991 ×305) and at least one enzyme Immunoassay (EIA) is available (Ryan-Poirier, K. A. et al, J. Clin. Microbiol., 1992 30 1072). A nxxuer of comparisons of these rapid detection methods for influenza A have been reported; see for example Leonardi, G. P. et al, J. Clin. Microbiol., 1994 32 70, who recommended that direct specimen testing be used together with culture isolation, so as to permit both identification of the virus, in time to institute therapy and infection control measures, and to monitor the antigenic constitution of influenza strains prevalent in the cotunity for epidemiological purposes. The IFA method is reported to be labor-intensive, and requires considerable technical expertise, with the results often being difficult to interpret. On the other hand, the EIA method (Directigen FLU-A; Becton Dickinson Microbiology Systems) gave a high level of false-positive results, and it has been recmmended that this assay should be used in laboratories only in addition to or as a substitute for direct immunofluorescence tests (Waner, J. L. et al, J. Clin. Microbiol., 1991 29 479).

As well as the problems mentioned above with the available rapid assays for influenza, there are other fundamental deficiencies in some of these methods. Firstly, none of the available assays can detect influenza B, which means that even a negative test result would leave the physician uncertain about the type of therapy that should be used. Secondly, if a rapid immunoassay method depends on the use of antibodies to one of the influenza A proteins, there may be a serious problem in detecting new strains of the virus which have undergone a drift or shift in the structure of the antigenic proteins. Influenza A is notorious for its propensity to undergo such changes.

Another type of rapid assay for influenza viruses has been described in a series of patent specifications (see for example Liav, A. et al, International Patent Application No. WO 92/12256). The method involves the use of a chromogenic substrate for the influenza neuraminidase enzyme. In other words the assay depends on visualising a dye, which is formed when the influenza neuraminidase cleaves a special sialic acid-dye conjugate molecule. This technique appears to offer limited specificity, because it could not readily distinguish between the presence of viral neuraminidase and other forms of the enzyme, particularly bacterial neuraminidase. It may also have low sensitivity because of the relatively slow activity of viral neuraminidase.

Neuraminidase is one of the key proteins present on the surface of the influenza virus, and it plays an important role in the ability of the virus to infect humn cells. It has long been thought that agents which bind to the neuraminidase enzyme might prevent infection by influenza, and much effort has gone into seeking such binders. Whilst many compounds have shown in vitro activity against influenza neuraminidase, only recently has it been established that it is possible to achieve protection from influenza infection in vivo by the use of a powerful neuram idase binder which binds to the active site of the enzyme (see von Itzstein, M. et al, Nature 1993 363 418 and our earlier patent applications, International Patent Applications No. WO 92/06691 and No. WO 91/16320, the entire disclosures of which are herein incorporated by this reference). In particular it has been found that 2,3-didehydro-2,4-dideoxy-4-guanidinyl-N-acetylneuraminic acid (Compound I, designated GG167) is a potent binder of influenza neuraminidase, and also shows potent in vivo antiviral activity in aniinl s (Ryan, D. M. et al, Antimicrobial Agents and Chemotherapy, 1994 38 2270) and in human volunteers (Hayden, P. G. et al, J. American Medical Assoc., 1996 275 295).

[Structure: cyclohexene with HO-CH(OH)-CH(OH)- at top, AcNH-, O in ring, CO2H, and HN-C(=NH)-NH2 guanidino group]

More recently it has been found that certain substituted cyclohexene derivatives of sialic acid are also potent binders of influenza virus neuraminidase (Kim, C. U. et al, J. Amer. Chem. Soc., 1997 119 681), and specifically the compound (3R,4R,5S)-4-acetamido-5-amino-3-(1-ethylpropoxy)-1-cyclohexene-1-carboxylic acid (GS 4071)

It is the purpose of the present invention to overcome some of the problems inherent in the prior art methods and to provide a simple and sensitive means of detecting influenza viruses.

Accordingly, we have now found that biologically active substances which possess stereochemical complementarity to the active site of influenza virus neuraminidase, as disclosed in the publication by von Itzstein et al referred to above, such that the $IC_{50}$ for binding is $10^{-6}$ M or less, and in particular certain derivatives of Compound I can be used to detect influenza virus through their ability both to selectively bind the influenza virus and at the same time to be attached to a surface or to a detectable linking group.

SUMMARY OF THE INVENTION

The invention therefore provides in a first aspect a method of detection of influenza virus, comprising the step of exposing a sample suspected to comprise said virus to a compound (neuraminidase binder) which is able to bind specifically to the active site of influenza virus neuraminidase, but which is not cleaved by neuraminidase.

The method of the invention is applicable to all known strains of influenza A and influenza B.

For the purposes of this specification it is to be clearly understood that the word "comprising" is to be understood to mean "including but not limited to". The words "comprise" and "comprises" are to be similarly understood.

Preferably the neuraminidase binder is linked via a spacer group to a surface or to a detectable label. The spacer group should be sufficiently long that the detectable label is exposed on the surface of the virus particle.

The method of the invention may use selective capture and concentration of the virus, followed by detection of the virus using any convenient conventional method; the detection method need not have inherent selectivity. For example, the neuraminidase binder may be attached to a support material, such as a membrane or polymer, such that virus particles will be selectively captured and concentrated when a sample is passed over or through the support. Therefore in one preferred embodiment of the invention, the spacer group temiiates in a functionality able to bind to a surface. Many suitable functionalities are known in the art. For example the terminal functionality may be a biotinyl group which can be used to attach the binder to a surface coated with avidin, streptavidin, or an antibody directed against biotin.

Alternatively the terminal functionality may for example be an amino group which can be used to conjugate the neuraminidase binder to a carboxy-comprising surface.

Alternatively, a selective detection approach may be used; the virus particles in a sample may for example be exposed to a neuraminidase binder coupled to a detectable label, under conditions such that the binder binds selectively to the viral neuraminidase on the surface of the viral particle. Preferably the detectable label is covalently coupled to the neuraminidase binder. The detectable label is then detected using any convenient method. For some detection systems, it is convenient to focus the sample into a confined area, for example a spot or a line on a surface. This may be achieved by a variety of methods; for example, the sample may be suspended or non-selectively captured on to a filter or other support material, and then exposed to the labelled neuraminidase binder as described above. There are several known methods for the non-selective capture of influenza virus, for example on a fetuin-coated surface (J. Virological Methods, 1992 39 111) or on a suitable membrane (J. Virological Methods, 1992 40 77). Another suitable detection system could be an optical assay device as described by Miller, B. J. et al, United States Patent Application No. 5,418,136.

In another, alternative, aspect the invention may use a combination of selective capture and selective detection to provide a simple and sensitive two-stage method of detecting influenza virus. This makes use of the fact that each influenza virus particle typically has about one hundred neuraminidase molecules spread over its spherical surface (White, D. O., Curr. Top. Microbiol. Immunol., 1974 63 1–48), and can therefore attach to more than one neuraminidase binder molecule at the same time.

Thus, a neuraminidase binder compound may be attached to a support, for example as a narrow band across a length of porous membrane. The test sample is then applied at the other end of the membrane and allowed to flow across the band of bound compound. Any influenza virus particles in the test sample will be trapped by the membrane-bound compound and thus retained in the narrow band. In the second stage of the test a detectable label attached to the neuraminidase binder is allowed to flow through the membrane across the band of bound influenza virus particles. The presence of influenza virus is then shown by an observable change in the membrane at the site of the bound compound. Suitable chromatographic assay devices have been described, for example by Chandler, H. M., International Patent Application No. WO 92/21977.

A very large number of suitable detection systems is known in the art, for example biotin-streptavidin, enzymic systems such as horseradish peroxidase or alkaline phosphatase, fluorescence systems, chemiluminescence systems, colloidal gold, radioactive labels and agglutination systems. It is contemplated that colloidal gold linked to a neuraminidase binder via a spacer group will be a particularly convenient detectable label. Another convenient detection system would utilize the neuraminidase binder covalently coupled to horseradish peroxidase. The skilled person will readily be able to select a suitable detection system and to optimise conditions for detection, using normal trial and error experimentation.

The neuraminidase binder may be any agent which binds to the active site of the influenza virus neuraminidase, provided that it does not comprise a detectable label or spacer group which is cleaved by the neuraminidase. The binding need not be irreversible. The $IC_{50}$ for binding is suitably $10^{-6}$ M or better.

Suitable agents include, but are not limited to, compounds of suitable $IC_{50}$ disclosed in our earlier patent applications, International Patent Applications No. WO 92/06691 and WO/91/16320, and also U.S. Pat. No. 5,453,533 by Luo et al, U.S. Pat. No. 5,512,596 by Gilead Sciences, Inc., and International Patent Application No. WO/96/26933 by Gilead Sciences, Inc. Although these specifications disclose the use of the compounds disclosed therein for treatment or prophylaxis of influenza virus infection, it is not suggested that the compounds are useful for diagnostic purposes, using assays of the type described herein.

According to a second aspect, the invention provides a neuraminidase binder suitable for use in the method of the invention, comprising an analogue of neuraminic acid (sialic acid) substituted at the $C_7$ or at an equivalent position on a branched side chain attached to the ring system of said analogue with a spacer group suitable for coupling to a detectable label or to a surface.

In a preferred embodiment, this aspect provides compounds of formula (II):

(II 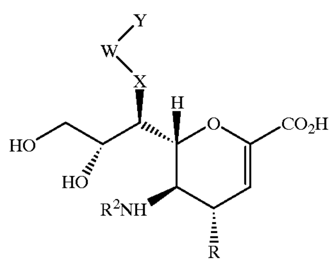 wherein

- R represents an azido group, an unsubstituted or substituted guanidino group, or an unsubstituted or substituted amino group;
- $R^2$ represents $COCH_3$, $COCF_3$ or $SO_2CH_3$;
- X represents O or NH;
- W represents a spacer group made up of a chain of atoms having a total length of between four and one hundred atoms, and optionally also comprising substituted carbon and/or nitrogen atoms and optionally including oxygen and/or sulphur atoms;
- Y represents OH, SR, $NH_2$, CH═O, CH═$CH_2$, $CO_2H$, $CONHNH_2$ or NH-biotinyl, or a protected form of one of these end functionalities;
- and wherein the substituent on the amino or guanidino group, when present, is a substituted or unsubstituted $C_{1-6}$ alkyl, such as a methyl or ethyl group or an aryl group such as phenyl; or an amino, hydroxy, cyano or alkoxycarbonyl group;
- with the proviso that X-W-Y does not include the group OC(═Z)$NR^5R^6$, wherein Z represents O or S, and $R^5$ and $R^6$ independently represents H or a hydrocarbon group optionally substituted by $NH_2$, OH or SH, but $R^5$ and $R^6$ are not both H.

In another preferred embodiment, the invention provides neuraminidase binders of formula (IIA) or (IIB)

(IIA)

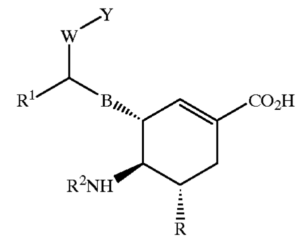

(IIB)

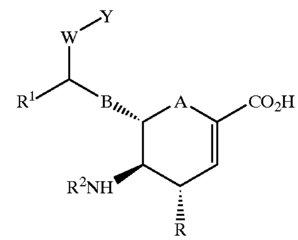

wherein R, $R^2$, W and Y are as defined above for formula (II), A and B are oxygen or $CH_2$ or may represent a single bond, and $R^1$ is a lipophilic $C_1$–$C_{12}$ alkyl group which is optionally substituted by one or more halogen atoms, cycloalkyl, alkoxy, haloalkoxy or optionally substituted aryl groups.

Suitable spacer groups W include, but are not limited to, linear peptides, oligosaccharides, polyols, polyethylene glycol groups, hydrocarbon groups and hydrocarbon groups linked together with oxygen or sulphur atoms or with carbonyl, amido, urea or hydrazide functionalities. Spacer groups W may also comprise combinations of these various groups.

Suitable protecting groups for the end functionality Y include, but are not limited to, esters of the OH, SH and $CO_2H$ groups, carbamates of the $NH_2$ and $CONHNH_2$ groups, and acetals of the CH═O group.

As used herein, the term "hydrocarbon group" includes saturated and unsaturated straight or branched hydrocarbon groups, including aryl groups, and cambinations of such groups.

Preferred compounds of the invention include compounds of formula (II) wherein R represents guanidino and $R^2$ represents acetyl.

Another group of preferred compounds of the invention of formula (II) are those wherein X is O and Y is $NH_2$ or NH-biotinyl.

A third preferred group of compounds of the invention includes neuraminidase binders of formula (IIA) in which R is amino, $R^2$ is acetyl, B is oxygen and $R^1$ is an alkyl group.

Further preferred compounds are those of formula (II) wherein W is a spacer group selected from the group consisting of $CONH(CH_2)_n$, $CONH(CH_2)_nNHCONH(CH_2)_m$, $CONH(CH_2)_n[NHCO(CH_2)_5]_m$, $CO(CH_2)_n$, $CO(CH_2)_nNHCONH(CH_2)_m$, $CO(CH_2)_nNHCO(CH_2)_q$, $CONH(CH_2)_nNHM(COCH_2NH)_qCOCH_2$; $CONH(CH_2CH_2O)_nCH_2CH_2NHCO(C_2)_q$, and $CONH(CH_2)_nNHCO(CH_2)_q$, wherein n and m are integers between 2 and 12, and q is 0 or an integer between 1 and 12.

The person skilled in the art will be able to select a suitable detectable label and detection system, and to test the compounds referred to above for their suitability using routine methods. Thus the skilled person would be able to choose a suitable detection system, such as selective capture or selective detection as described above. For selective capture systems, the spacer group will terminate in a functionality able to bind to a solid support. Many suitable functionalities are known in the art.

The substitution by the group W-Y at $C_7$ (or equivalent) should not decrease the ability of the parent compound to bind to neuraminidase by a significant extent; preferably the binding is not decreased more than 100-fold. The ability to bind to neuraminindase may be assessed using any convenient method; one suitable method is the in vitro bioassay of neuraminidase activity described by Warner and O'Brien, Biochemistry, 1979 18 2783–2787. In vitro bioassay is described in our Application No. WO 91/16320. Alternatively binding of a radioactively-labelled binder compound to neuraminidase can be assessed by methods known in the art.

Suitable types of clinical samples for use in the method of the invention include throat swabs, nasal swabs, nasopharyngeal washings, nasal washes and gargles, or combinations of any of these; the gargles may optionally bet concentrated, for example by ultracentrifugation, if necessary, but it is expected that this will only be the case when the number of viral particles is low.

It will be clearly understood that the label which is linked to the spacer group may be an epitope suitable for use in antibody detection kits, such as those described in U.S. Pat. No. 4,943,522 by Eisinger et al (assigned to Quidel); in optical assay devices having an active receptive surface, such as those described in U.S. Pat. No. 5,418,136 by Miller et al (assigned to Biostar, Inc.); or in agglutination detection systems such as those described in U.S. Pat. No. 4,894,347 and International Patent Application No WO 91/04492, both by Agen Limited. It is also contemplated that biosensor systems are suitable for use in the method of the invention. For example, a carbohydrate biosensor surface for detection of bacteria has been described (Nilsson, K. G. I. and C. F. Mandenius; BioTechnology, 1994 12 1376–1378).

Some compounds according to the invention bind particularly strongly to influenza virus neuraminidase, with $IC_{50}$ of $10^{-8}$ M or better, and these compounds may also be therapeutically useful.

The compounds of the invention may be prepared by a variety of methods, and in a further aspect of the invention provides methods for the preparation of compounds of formula (II). In one type of approach the preparation of the compounds of the invention wherein X is O may be carried out as shown in the reaction schemes below in which R, $R^2$ and Y are as defined for formula (II), R' is an alkyl group and W' is a spacer group. Thus, a sialic acid derivative of formula (III) is converted into the 8,9-protected form of formula (IV), which may be for example a cyclic carbonate (A=C=O) or an acetonide (A=$CMe_2$). The remaining free 7-hydroxy group is acylated with either an isocyanate group OCN—W'—Y or an acyl chloride (ClCOL), which has a second leaving group L, the group L then being displaced by an amine $H_2N$—W'—Y. The group W' is a spacer group, generally of 4 to 10 atoms length, generally within the definition of W' and W may be equivalent to CONHW'. The spacer group We can be further extended or functionalised, for example by the addition of biotin to the end of the chain as in (VI).

Finally, the protecting groups A, R' and any that are present on the substituents R and Y, can be removed under standard conditions to give the compounds of formula (II). A variety of protecting groups suitable for protection of the hydroxy and carbonyl groups is known in the art; see for example "Protecting Groups in Organic Synthesis" by T. H. Greene (Wiley & Sons, 1981).

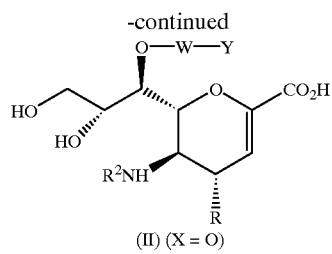

(II) (X = O)

Compounds of formulae (III) and (IV) are known, and their preparation has been described, for example, in International Patent Application No. WO 91/16320.

Another type of approach for the preparation of compounds of the invention wherein X is NH involves starting with a sialic acid derivative and carrying out reactions which give a double inversion at the C7 position. For example, an intermediate of general formula (IV) may be reacted under Mitsunobu Reaction conditions to give a suitable leaving group ester with inverted stereochemistry at C7 (Anderson, N. G. et al, J. Org. Chem., 1996 61 7955). Displacement of the C7 ester with a nucleophile such as azide then gives a C7 nitrogen substituted derivative with the correct stereochemistry. An alternative method for the introduction of nitrogen to the C7 position of sialic acid derivatives has been described (Kong and von Itzstein, Tetrahedron Letters, 1995 36 957).

Most of the intermediates of formula (V) and (VI) are novel compounds, and these comprise a further aspect of the present invention.

DETAILED DESCRIPTION OF THE INVENTION

The invention will now be described in detail by way of reference only to the following non-limiting examples.

Examples of compounds of the invention of formula (II) (X=O) are shown in Table 1. Those examples of substituent Y which include biotin have the biotin attached via an amide linkage to its carboxy group.

TABLE 1

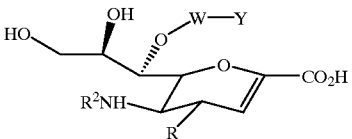

| Compound No. | R | $R^2$ | W | Y |
|---|---|---|---|---|
| 8 | NHC(=NH)NH$_2$ | Ac | CONH(CH$_2$)$_6$NHCONH(CH$_2$)$_6$ | NH$_2$ |
| 11 | NHC(=NH)NH$_2$ | Ac | CONH(CH$_2$)$_6$ | NH$_2$ |
| 13 | NHC(=NH)NH$_2$ | Ac | CONH(CH$_2$)$_6$ | NHBoc |
| 17 | NHC(=NH)NH$_2$ | Ac | CONH(CH$_2$CH$_2$O)$_2$CH$_2$CH$_2$ | NH$_2$ |
| 19 | NHC(=NH)NH$_2$ | Ac | CONH(CH$_2$)$_6$ | NH-Biotin |
| 20 | NH$_2$ | Ac | CONH(CH$_2$)$_6$NHCONH(CH$_2$)$_6$ | NHBoc |
| 21 | NHC(=NH)NH$_2$ | Ac | CONH(CH$_2$)$_6$(NHCOCH$_2$)$_3$ | NH-Biotin |
| 22 | NHC(=NH)NH$_2$ | Ac | CONH(CH$_2$)$_6$NHCO(CH$_2$)$_{11}$ | NH-Biotin |
| 23 | NHC(=NH)NH$_2$ | Ac | CONH(CH$_2$)$_6$NHCO(CH$_2$)$_5$ | NH-Biotin |
| 25 | NHC(=NH)NH$_2$ | Ac | CONH(CH$_2$)$_6$[NHCO(CH$_2$)$_5$]$_4$ | NH$_2$ |
| 26 | NHC(=NH)NH$_2$ | Ac | CONH(CH$_2$)$_6$[NHCO(CH$_2$)$_5$]$_4$ | NH-Biotin |
| 27 | NHC(=NH)NH$_2$ | Ac | CONH(CH$_2$)$_6$NHCO(CH$_2$)$_5$NHCOCH$_2$(OCH$_2$CH$_2$)$_{16}$ | NH-Biotin |
| 28 | NHC(=NH)NH$_2$ | Ac | CONH(CH$_2$)$_6$[NHCO(CH$_2$)$_5$]$_2$ | NH$_2$ |
| 29 | NHC(=NH)NH$_2$ | Ac | CONH(CH$_2$)$_6$[NHCO(CH$_2$)$_5$]$_4$NH—COCH$_2$CH$_2$ | CONHNHBoc |
| 30 | NHC(=NH)NH$_2$ | Ac | CONH(CH$_2$)$_6$[NHCO(CH$_2$)$_5$]$_4$NH—COCH$_2$CH$_2$ | CONHNH$_2$ |
| 31 | NHC(=NH)NH$_2$ | Ac | CONH(CH$_2$)$_6$NHCOCH$_2$CH$_2$ | CO$_2$H | and examples of intermediates of formula (V) and (VI) are given in Table 2. Again Boc represents butoxycarbonyl.

TABLE 2

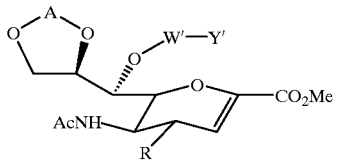

| Compound No. | A | R | W' | y' |
|---|---|---|---|---|
| 3 | C=O | N₃ | CONH(CH₂)₆ | NHBoc |
| 4 | C=O | N₃ | CONH(CH₂)₆ | NH₂ |
| 5 | C=O | N₃ | CONH(CH₂)₆NHCONH(CH₂)₆ | NHBoc |
| 6 | C=O | NH₂ | CONH(CH₂)₆NHCONH(CH₂)₆ | NHBoc |
| 7 | C=O | NHC(=NH)NH₂ | CONH(CH₂)₆NHCONH(CH₂)₆ | NHBoc |
| 9 | C=O | NH₂ | CONH(CH₂)₆ | NHBoc |
| 10 | C=O | NHC(=NBoc)NHBoc | CONH(CH₂)₆ | NHBoc |
| 12 | C=O | NHC(=NH)NH₂ | CONH(CH₂)₆ | NHBoc |
| 14 | C=O | N₃ | CONH(CH₂CH₂O)₂CH₂CH₂ | NHBoc |
| 15 | C=O | NH₂ | CONH(CH₂CH₂O)₂CH₂CH₂ | NHBoc |
| 16 | C=O | NHC(=NBoc)NHBoc | CONH(CH₂CH₂O)₂CH₂CH₂ | NHBoc |
| 18 | C=O | NHC(=NH)NH₂ | CONH(CH₂)₆ | NH₂ |
| 24 | C=O | NHC(=NH)NH₂ | CONH(CH₂)₆[NHCO(CH₂)₅]₄ | NHBoc |
| 32 | C=O | NHC(=NH)NH₂ | CONH(CH₂)₆NHCOCH₂CH₂ | CO₂H |

EXAMPLE 1

Preparation of 5-acetamido-7-[6'-(6"-aminohexylureido)-hexyl]-carbamoloxy-4-guanidino-2,3,4,5-tetradeoxy-D-glycero-D-galacto-non-2-enopyranasonic acid (8)

(A) Preparation of methyl 5-acetamido-4-azido-8,9-monocarbonyldioxy-2,3,4,5-tetradeoxy-D-glycero-D-galacto-non-2-enopyranosonate (2).

To a suspension of methyl 5-acetamido-4-azido-2,3,4,5-tetradeoxy-D-glycero-D-galacto-non-2-enopyranosonate (1) (1.32 g, 4.03 mmol) in dry dichloromethane (32 ml) and acetonitrile (16 ml) containing N,N-dimethylaniline (1.6 ml, 12.46 mmol) in an ice-bath under argon, was added dropwise a 20% solution of phosgene in toluene (3 ml, 6.06 mmol) over a period of 20 min. The clear reaction mixture was stirred at ice-bath temperature for 2 hr. then left at roam temperature for 16 hr before being evaporated to dryness. the residue was partitioned between ethyl acetate (300 ml) and water (50 ml). The organic layer was washed successively with 0.5 M HCl solution (32 ml) at 5–10° C., saturated sodium chloride solution (3×30 ml), dried over anhydrous Na₂SO₄, then evaporated to dryness. The residue was subjected to flash column chromatography (silica gel, ethyl acetate/hexane=8/1) to afford compound (2) (1.035 g, 71%) as a white foam.
MS (FAB): 357 (M+1)⁺
i.r. (CHCl₃) cm⁻¹: 3314,2101,1774,1734,1654.
¹H-nmr (CDDl₃) δ (ppm): 2.13 (s, 3H), 3.81 (s, 3H), 3.82 (d, 1H) 3.90 (d, 1H), 4.08 (dd, 1H), 4.21 (dd, 1H), 4.72 (d, 2H), 4.97 (ddd, 1H), 5.95 (d, 1H), 6.55 (d, 1H).

(B) Preparation of methyl 5-acetamido-4-azido-7-(6'-tert-butoxycarbonylaminohexyl)-carbamoyloxy-8,9-monocarbonyldioxy-2,3,4,5-tetradeoxy-D-glycero-D-galacto-non-2-enopyranosonate (3)

To a solution of compound (2) (577 mg, 1.62 mmol) in anhydrous pyridine (8 ml) under argon, was added 4-dimethylaminopyridine (DMAP) (275 mg, 2.25 mmol) and 4-nitrophenyl chloroformate (424 mg, 2.11 mmol). The reaction mixture was stirred at 30–35° C. for 3.5 hr. To this mixture was added 6-tert-butoxycarbonylaminohexylamine (567 mg, 2.63 mmol) and DMP (405 mg, 3.32 mmol). The mixture was stirred at room temperature under argon for 24 hr then diluted with ethyl acetate (400 ml). The ethyl acetate solution was washed successively with water (3×40 ml), 2M HCl (40 ml) at 5–30° C. and then water (3×20 ml). The organic layer was evaporated to dryness to give the crude product (1.103 g) which was then flash chrcmatographed (silica gel, firstly, ethyl acetate/hexane =2/1, secondly ethyl acetate) to afford the title compouncL (3) (726 mg, 75%) as a white foam.
MS (FAB): 599(M+1)⁺,607(m+9)⁺, (M+1+2H₂O—N₂)
i.r. (CHCl₃) cm⁻¹: 3328, 2734, 2099, 1799, 1732, 1682.
¹H-nmr (CDCl₃) δ (ppm): 1.20–1.40 (m, 4H), 1.40–1.60 (m, 13H), 2.07 (s, 3H), 3.01–3.42 (m, 5H), 3.84 (a, 3H), 4.50–4.85 (m, 4H), 4.93 (m, 2H), 5.03 (m, 1H), 5.41 (m, 1H), 5.95 (d, 1H). 6.48 (d, 1H).

(C) Preparation of methyl 5-acetamido-7-[6'-(6"-tert-butoxycarbonylaminohexylureido)-hexyl]-carbamoyloxy-4-azido-8,9-monocarbonyldioxy-2,3,4,5-tetradeoxy-D-glycero-D-galacto-non-2-enopyranosonate (5).

A solution of compund (33 (200 mg, 0.334 mmol) in trifluoroacetic acid (2 ml) was stirred under argon at room temperature for 1 hr, then evaporated under reduced pressure to dryness. The residue was taken up in methanol (5 ml) and evaporated to dryness again to give compound (4) as a white foam.
¹H-nmr (CDCl₃) δ (ppm): 1.25–1.70 (m, 8H), 2.08 (s, 3H), 3.0–3.5 (m, 4H), 3.81 (s, 3H), 3.88 (dd, 1H), 4.4–4.8 (m, 4H), 5.01 (ddd, 1H), 5.30 (dd, 1H), 5.51 (dd, 1H), 5.86 (d, 1H), 6.73 (d, 1H), 7.34 (d, 1H).
Compound (4) was then dissolved in pyridine (2 ml) containing a mixture of DMAP (30 mg, 0.246 mmol) and 6-tert-butoxycarbhnylaminohexyl isocyanate (0.15 ml, 0.434 mmol). The reaction mixture was stirred under argon at 18–20° C. for 72 hr, then stirred with methanol (0.2 ml) at room temperature for 3 hr. The resulting reaction mixture was evaporated to dryness and partitioned between ethyl acetate (200 ml) and 1M $NaH_2PO_4$ solution (50 ml). The organic layer was washed successively with 1M $NaH_2PO_4$ (2×50 ml), water (3×25 ml) and vacuum evaporated to dryness. The residue was flash-chromatographed (silica gel, using ethyl acetate/hexane=8/1, then ethyl acetate/methanol=10/1) to afford the title compound (5) (180 mg, 72%) as a white foam.

MS (FAB): 741 $(m+1)^+$, 749 $(m+9)^+$ i.r. $(CHCl_3)$ $cm^{-1}$: 3356, 2934, 2098, 1801, 1732, 1654.

$^1$H-nmr $(CDCl_3+CD_3OD)$ δ(ppm): 1.12–1.42 (m, 25H), 1.80 (s, 3H), 2.90–3.18 (m, 9H), 3.70 (s, 3H), 3.90 (dd, 1H), 4.18 (dd, 1H), 4.32 (dd, 1H), 4.55 (d, 2H), 4 91 (m, 1H), 5 21 (br, 1H), 5.35 (dd, 1H), 5.45 (br d, 1H), 5. 82 (d, 1H), 6.05 (dd, 1H), 7.82 (d, 1H).

(D) Preparation of methyl 5-acetamido-4-amino-7-[6'-(6"-tert-butoxycarbonyl aminohexylureido)-hexyl]-carbmoyloxy-8,9-monocarbonyldioxy-2,3,4,5-tetradeoxy-D-glycero-D-galacto-non-2-enopyranosonate (6).

A mixture of compound (5) (180 mg, 0.246 mmol) acetic acid (35 mg, 0.58 mmol) and Pd/C (10%) (30 mg) was agitated in a mixture of methanol (10 ml) and toluene (6 ml) under hydrogen at room temperature for 1 hr. The reaction mixture was filtered through Celite, the filter-cake was washed with methanol (30 ml) and the filtrate and washings were combined and vacuum evaporated to dryness. The residue was subjected to flash column chromatography (silica gel, ethyl acetate/2-propanol/water=5/2/1) to afford compound (6) (46 mg, 47.5%) as a white foam, as well as recovered starting material (80 mg, 44%).

$^1$H-nmr $(CD_3OD)$ δ(ppm): 1.15–1.55 (m, 25H), 1.87 (s, 3H, AcOH), 1.92 (s, 3H), 2.90–3.10 (m, 8H), 3.56 (dd, 1H), 3.69 (s, 3H), 3.91 (dd, 1H), 4.20 (dd, 1H), 4 62 (d, 2H), 5.05 (dd, 1H), 5.46 (dd, 1H), 5.85(dd, 1H).

(E) Preparation of methyl 5-acetamido-7-[6'-(6"-tert-butoxycarbonylaminohexylureido)-hexyl]-carbamoyloxy-4-[2,3-bis(tert-butoxycarbonyl]-guanidino-8,9-monocarbonyl-dioxy-2,3,4,5-tetradeoxy-D-glyco-D-galacto-non-2-enopyranosonate(7).

A solution of compound (6) (46 mg, 0.065 mmol) in methanol (10 ml) was treated with Amberlite IRA-400 (OH) resin (100 mg) for 30 seconds and filtered off. The resin was washed with methanol (20 ml). The filtrate and washing were coubined, evaporated to dryness to give 41 mg solid substance which was then mxed with N,N'-bis-tert-butoxycarbonyl-1H-pyrazole-1-carboxamidine (103 mg, 0.332 mmol) in methanol (5 ml). The mixture was stirred under argon at 30–35° C. for 5 days, then evaporated to dryness. The residue was flash chromatographed (silica gel, first ethyl acetate/hexane=8/1, then, ethyl acetate) to give compound (7) (47 mg, 88.8%) as a white foam.

i.r. $(CHCl_3)$ $cm^{-1}$: 3312, 2933, 1802, 1728, 1643, 1564.

$^1$H-nmr $(CDl_3($ δ(ppm): 1.20–1.60 (m, 43H), 1.87 (s, 3H), 2.19 (s, 1H), 2.90–3.20 (m, 8H), 3.73 (9, 3H), 4.17 (dd, 1H), 4.33 (br d, 1H), 4.53–5.20 (m, 8H), 5.51 (br, 1H), 5.38 (d, 1H), 6.66 (br, 1H), 8.38 (d, 1H).

(F) Preparation of 5-acetamido-7-[6'-(6"-aminohexylureido)-hexyl]-carbamoyloxy-4-guanidino-2,3,4,5-tetradeoxy-D-glycero-D-galacto-non-2-enopyranosonic acid (8).

A solution of compound (7) (47 mg, 0.058 mmol) in a mixture of methanol (5 ml) and water (5 ml) containing triethylamine (0.8 ml) was stirred under argon at room temperature for 6 hr, then evaporated under reduced pressure to dryness. The residue was dissolved in a mixture of methanol (5 ml) and water (5 ml), then stirred with Dowex 50WX8S($H^+$) resin (1 g) at room temperature for 1 hr. The resin was filtered and washed with a mixture of methanol and water (1:1), then stirred with 2M $N_4OH$ solution (20 ml) at room temperature for 2 hr and filtered off. The filtrate was evaporated to dryness. The residue was redissolved in water (5 ml) and evaporated to dryness again. The resulting solid was dissolved in water (2 ml) and freeze-dried to afford compound (8) (16 mg, 45.7%) as a white solid with a positive guanidine (Sakaguchi) reaction.

MS (FAB): 617 $(M+1)^+$ $^1$H-nmr $(D_2O)$ δ(ppm):1.10–1.17 (m, 18H), 2.07 (s, 3H), 2.85–3.20 (m, 6H), 3.50 (dd, 1H), 3.70 (dd, 1H), 4.10 (m, 2H), 4.45 (dd, 1H), 4.52 (dd, 1H), 4.95 (dd, 1H), 5.65 (d, 1H).

EXAMPLE 2

Preparatioan of 5-acetamido-7- (6'-aminohexyl)-carbomoyloxy-4-guanidino-2,3,4,5-tetradeoxy-D-glycero-D-galacto-non-2-enopyranosonic acid as trifluortoacetic acid salt (11)

(A) Preparation of methyl 5-acetamido-4-amino-7-(6'-tert-butoxycarbonylaminohexyl)-carbamoyloxy-8,9-monocarbonyldioxy-2,3,4,5-tetradeoxy-D-glycero-D-galacto-non-2-enopyranosonate (9).

Compound (3) (Example 1, part (B) (500 mg, 0.836 mmol) was hydrogenated, according to the procedure described in Example 1, part (D) to afford compound (9) (285 mg, 59.6%) as a white foam.

MS (FAB): 573 $(M+1)^+$ i.r. $(CHCl_3)$ $cm^{-1}$: 3385, 2935, 1794, 1725, 1670, 1542.

$^1$H-nmr $(CD_3OD)$ δ (ppm): 1.15–1.48 (m, 17H), 1.91 (s, 3H), 2.96 (m, 4H), 3.51 (dd, 1H), 3.70 (s, 3H), 3.88 (dd, 1H), 4.21 (dd, 1H), 4.62 (d, 2H), 5.05 (ddd, 3H), 5.45 (dd, 1H), 5.87 (d, 1H).

(B) Preparation of methyl 5-acetamido-7-(6'-tert-butoxycarbonylaminohexyl)-carbamoyloxy-4-[2',3"-bis(tert-butoxycarbonyl)]-guanidino-8,9-monocarbonyldioxy-2,3,4,5-tetradeoxy-D-glycero-D-galacto-non-2-enopyranosonate (10).

The title compound (10) (149 mg, 83.4%) was obtained as a white foam from compound (9) (125 mg, 0.219 mmol) following the procedure described in Example 1, part (E).

MS (FAB): 815 $(M+1)^+$ i.r. $(CHCl_3)$ $cm^{-1}$: 3313, 2978, 1805, 1727, 1643, 1610, 1558.

$^1$H-nmr $(CDCl_3)$ δ (ppm): 1.11–1.82 (m, 35H), 1.91 (s, 3H), 2.98–3.21 (m, 4H), 4.13 (dd, 1H), 4.32 (dd, 1H), 4.50–4.80 (m, 3H), 4.91–5.22 (m, 3H), 5.45 (dd, 1H), 5.89 (d, 1H), 6.69 (br d, 1H), 7.63 (d, 1H), 8.48 (d, 1H).

(C) Preparation of 5-acetamido-7-(6'-aminohexyl)-carbamoyloxy-4-guanidino-2,3,4,5-tetradeoxy-D-glycero-D-galacto-non-2-enopyranosonic acid as trifluoroacetic acid salt (11).

Compound (10) (54 mg, 0.066 mmol) was stirred in a mixture of methanol (25 ml) and water (25 ml) containing triethylamine (5 ml) under argon at room temperature for 6 hr then evaporated under vacuum to dryness. The residue was chromatographed (silica gel, ethyl acetate/2-propanol/ water=5/2/1) and the fractions with $R_f$ value of 0.4 were combined and-evaporated to dryness. The residue was stirred in trifluoroacetic acid (2 ml) under argon at room temperature for lhr then evaporated to dryness. The residue was dissolved in water (3 ml) and freeze-dried to afford the title compound (11) (27 mg, 69%).
MS (FAB): 475 $(M+1)^+$, 589 $(M+1+TFA)^+$.
$^1$H-nmr ($D_2O$) δ (ppm): 1.27–1.81 (m, 8H), 1.98 (s, 3H), 2.89–3.21 (m, 4H), 3.51 (dd, 1H), 3.69 (dd, 1H), 4.04 (m, 1H), 4.18 (dd, 1H), 4.46 (dd, 1H), 4.57 (dd, 1H), 4.96 (dd, 1H), 6.01 (d, 1H).

EXAMPLE 3

Preparation of 5-acetamido-7-(6'-tert-butoxycarbonylaminohexyl)-carbamoyloxy-4-guanidino-2,3,4,5-tetradeoxy-D-glycero-D-galacto-non-2-enopyanosmonic acid (13).

To a solution of compound (9) (24 mg, 0.042 mmol) in water (5 ml) was added 1H-pyrazole-1-carboxamidine (44 mg, 0.30 mmol) and imidazole (43 mg, 0.63 mmol) at room temperature. The resulting mixture was stirred under argorn at 90–95° C. for 22 hr, then evaporated to dryness to give crude compound (12) which gave a strong positive Sakaguchi reaction, indicating the presence of a guanidine group. The residue was stirred in water (5 ml) containing triethylminme (0.5 ml) under argon at room temperature for 16 hr before evaporating to dryness. The residue was subjected to chromatography (silica gel, 2-propanol/water=3/1). The fractions with $R_f$ value of 0.2 were combined and evaporated to dryness, then freeze-dried to afford the title compound (13) (9 mg, 37%) as a white solid
MS (FAB): 575 $(M+1)^+$
$^1$H-nmr ($D_2O$) δ (ppm): 1.25–1.83 (m, 17H), 1.95 (s, 3H), 2.95–3.25 (m, 4H), 3.52 (dd, 1H), 3.63 (dd, 1H), 3.72 (dd, 1H), 3.98 (dd, 1H), 4.10 (m, 1H), 4.46 (dd, 1H), 4.52 (dd, 1H), 5.62 (d, 1H).

EXAMPLE 4

Preparation of 5-acetamido-7-{2-[2-(2-aminoethoxy)-ehtocy]-ethyl}-carbamoyloxy-4-guanidino-2,3,4,5-tetradeoxy-D-glycero-D-galacto-non-2-enopyranosonic acid (17)

(A) Preparation of methyl 5-acetamido-4-azido-7-{2'-[2"-(2"-tert-butoxycarbonylaminoethoxy]-ethoxy-ethyl}-carbamoyloxy-8,9-monocarbonyldioxy-2,3,4,5-tetradeoxy-D-glycero-D-galacto-non-2-enopyranosonate (14).

Following a similar procedure to that described in Example I, part (B) compound (14) (420 mg, 67%) was obtained as a white foam from compound (2) (356 mg, 1 mmol) and 2-[2'-(2"-tert-butoxycarbonylamino-ethoxy) ethoxy}-ethylamine.
MS (FAB): 631 $(M+1)^+$ 639 $(M+9)^+$
i.r. ($CHCl_3$) $cm^{-1}$: 3328, 2934, 2099, 1802, 1734, 1658, 1537.
$^1$H-nm ($CDCl_3$) δ (ppm): 1.41 (s, 9H), 1.97 (s, 3H), 3.12–3.64 (m, 12H), 3.78 (s, 3H), 4.41–4.71 (m, 4H), 5.01 (d, 2H), 5.12 (m, 1H), 5.43 (dd, 1H) 5.67 (br, 1H), 5.91 (d, 1H), 6.83 (br d, 1H).

(B) Preparation of methyl 5-acetamido-4-amino-7-{2'-[2"-(2"'-tert-butoxycarbonylaminoethoxy)-ethoxy]-ethyl}carbamoyloxy-8,9-monocarbonyldioxy-2,3,4,5-tetradeoxy-D-glycero-D-galacto-non-2-enopyranosonate (15).

Catalytic-hydrogenation of compound (14) (400 mg, 0.634 mmol), as described in Example I, part (D) afforded compound (15) (144 mg, 37.5%) as a white foam after chromatography (silica gel, ethyl acetate/2-propanol/water =5/2/1).
$^1$H-nmr ($CD_3O$) δ (ppm): 1.32 (s, 9H), 1.82 (s, 3H), 1.89 (s, 3H, AcOH), 3.04–3.22 (m, 4H), 3.36–3.53 (m, 8H), 3.68 (s, 3H), 3.72 (br d, 1H), 3.98 (dd, 1H), 4.25 (dd, 1H), 4.62 (d, 2H), 5.03 (ddd, 1H), 5.43 (dd, 1H), 5.84 (d, 1H).

(C) Preparation of methyl 5-acetamido-7-{2'-[2"-(2"'-tert-butoxycarbonylaminoethoxy)-ethoxy]-ethyl}-carbamoyloxy-4-[2',3"-bis(tert-butoxycarbonyl)]-guanidino-8,9-mono-carbonyldioxy-2,3,4,5-tetradeoxy-D-glycero-D-galacto-non-2-enopyranosonate (16).

Compound (15) (101 mg), 0.167 mmol) was guanidinated by the procedure described in Example I, part (E) to give comound (16) (72 mg, 51%) as a white foam.
$^1$H-nmr ($CDCl_3$) δ (ppm): 1.42 (s, 9H), 1.49 (br s, 18H), 1.89 (s, 3H), 3.12–3.65 (m, 12H), 3.78 (s, 3H), 4.07 (m, 1H), 4.32 (br d, 1H), 4.55–4.75 (m, 2H), 4.90–5.35 (m, 3H), 5.40–5.68 (m, 2H), 5.91 (d, 1H), 6.38 (d, 1H), 8.42 (d, 1H).

(D) Preparation of 5-acetamido-7-{2 '-[2 "-(2"'-aminoethoxy)-ethoxy]-ethyl}-carbuoyloxy-4-guanidino-2,3,4,5-tetradeoxy-D-glycero-D-galacto-non-2-enopyranosonic acid (17).

De-protection of compound (16) (70 mg, 0.082 mmol) by the procedure described in Example I, part (F) afforded the title compound (17) (25 mg, 60%) as a white solid which gave a positive Sakaguchi reaction.
MS (FAB): 507 $(M+1)^+$
$^1$H-nmr ($D_2O$) δ (ppm) : 1.96 (s, 3H), 3.14–3.78 (m, 14H), 4.12 (m, 2H), 4.41 (dd, 1H), 4.52 (dd, 1H), 4.93 (dd, 1H), 5.68 (d, 1H).

EXAMPLE 5

Preparation of 5-acetamido-7-(6'-biotinylaminohexyl)-carbamoloxy-4-guanidino-2,3, 4,5-tetradeoxy-D-glycero-D-galacto-non-2-enopyranosonic acid (19)

Compound (10) (176 mg, 0.216 mmol) was stirred in trifluoroacetic (5 ml) under argon at room temperature for 1 hr, then vacuum evaporated to dryness to afford compound (18) which was then allowed to react with N-hydroxysuccinimide ester of biotin (110 mg, 0.324 mmol) in aqueous acetone (7.5 ml of water and 15 ml of acetone) containing a mixture of $NaHCO_3$ (27 mg, 0.32 mmol) and $Na_2CO_3$ (34 mg, 032 mmol) at room temperature for 3 hr. The resulting mixture was evaporated to dryness. The residue was stirred in a mixture of methanol (25 ml) and water (25 ml) containing triethylsmine (4 ml) under argon at room temperature for 16 hr. The mixture was vacuum evaporated to dryness and the residue was subjected to chromatographlk (firstly, ethyl acetate/2-propanol/water =5/2/1, then 2-propanol/water =3/1). The fractions with $R_f$ value of 0.25 in the second solvent system were collected and evaporated to dryness.

The residue was dissolved in water and treated with Dowex 50×8($H^+$) resin (0.5 g) for 0.5 hr at room temperature. The resin was washed successively with water (50 ml), methanol (20 ml), water (10 ml), then eluted with 2M$NH_4OH$. The eluate was evaporated to dryness and freeze-dried to afford the title compound (19), (60 mg, 39.7%) as a white foam, which gave a positive Sakaguchi reaction.

MS (FAB): 701 (M+1)$^+$
i.r. cm$^{-1}$: 3330, 2934, 1674, 1616, 1429.
$^1$H-nmr (D$_2$O) δ (ppm): 1.25–1.80 (m, 14H), 2.01(s, 3H), 2.23 (dd, 2H), 2.78 (d, 1H), 2.98 (dd, 1H), 3.08–3.26 (m, 4H), 3.35 (m, 1H), 3.51 (dd, 1H), 3.68 (dd, 1H), 4.02–4.28 (m, 2H), 4.32–4.08 (m, 4H), 4.92 (dd, 1H), 5.76 (d, 1H).

EXAMPLE 6

Preparation of 5-acetamido-4-amino-7-[6'-(6"-tert-butoxycarbony-aminohexylureido)-hexyl]-carbamoyloxy-2,3,4,5-tetradeoxy-D-glycero-D-galacto-non-2-enopyanosonic acid (20)

Compound (6) (50 mg, 0.07 mmol) was stirred in a mixture of methanol (30 ml) and water (15 ml) containing triethylamine (4 ml) under argon at room temperature for 16 hr. The resulting mixture was vacuum evaporated to dryness. The residue was chromatographed (silica gel 2-propanol/water=3/1) to afford the title compound (20) (30 mg, 63.5%) as a white foam.
MS (FAB): 675 (M+1)$^+$
i.r. cm$^{-1}$:3333, 2932, 1710, 1633, 1557.
$^1$H-nmr (D$_2$O) δ (ppm): 1.22–1.57 (m, 25H), 1.98 (s, 3H), 2.98–3.18 (m, 8H), 3.49 (dd, 1H), 3.64 (dd, 1H), 4.02–4.28 (m, 3H), 4.53 (br d, 1H), 4.92 (dd, 1H), 5.72 (d, 1H).

EXAMPLE 7

Preparation of 5-acetamido-7-(6'-biotinylamino-triglycinamido-hexyl)-carbamoyloxy-4-guanidino-2,3,4,5-tetradeoxy-D-glycero-D-galacto-non-2-enopyranosonic acid (21)

To a solution of 6-biotinylaminotriglycine (101.2 mg, 0.24 ml) in a mixture of water (0.4 ml) and acetone (4 ml) at −10° were added successively triethylamine (24.6 mg, 0.24 mol), N-methylmorpholine (7 mg, 0.06 =mol) and isobutyl chloroformate (35 mg, 0.256 mmol). The whole mixture was stirred under argon at −10° for 12 min. before being combined with a solution of compound (18) (92 mg, 0.156 mmol) in a miture of water (1 ml) and acetone (1 ml) containing triethylamine (24.6 mg, 0.24 mmol) at 0–5°. The resulting reaction mixture was allowed to stir at 15–20° for 4 hr and then evaporated under reduced pressure to dryness. The residue was taken up in acetone (2×25 ml) and filtered to give a solid (69 mg) which was then stirred in a mixture of methanol (10 ml) and water (10 ml) containing triethylaminie (5 ml) under argon at room temperature for 16 hr. The solution was evaporated to dryness and redissolved in water (20 ml) and then evaporated to dryness again. This procedure was repeated five times to produce crude compound (21) (60 mg), which was then subjected to flash column chromatography (silica gel, firstly 2-propanol/water=5/1, and then secondly 2-propanol/water=3/1) to afford the title compound (21) (17 mg, 12.5%) as a white solid which gave a positive Sakaguchi reaction (guanidine colour reaction) and a positive biotin colour reaction.
MS (FAB): 872 (M+1)$^+$, 871 (M$^+$)
i.r. cm$^{-1}$: 3287 (br), 1651 (br).
$^1$H-nmr (D$_2$O) δ (ppm): 1.22–1.81 (m, 14H), 1.98 (s, 3H), 2.37 (m, 2H), 2.78 (d, 1H), 2.95–3.55 (m, 7H), 3.61–4.16 (m, 9H), 4.39–4.67 (m, 4H), 4.92 (dd, 1H), 5.67 (d, 1H).

EXAMPLE 8

5-Acetamido-7-(6'-biotinylamino-dodecanoyl-aminohexyl)-carbamoyl-4-guanidino-2,3,4,5-tetradeoxy-D-glycero-D-galacto-non-2-enopyranosonic acid (22)

This compound was prepared by coupling of biotinylaminododecanoic acid and compound (18) using carbonyl diimidazole, as described in Methods in Enzymology, 1990 184 664.

$^1$H-nmr (CD$_3$OD) δ (ppm): 1.28–1.85 (m, 33H), 1.98 (s, 3H), 2.22 (m, 4H), 2.75 (d, 1H), 2.97 (dd, 1H), 3.03–3.28 (m, 6H), 3.49 (dd, 1H), 3.64 (dd, 1H), 4.07 (m, 1H), 4.20 (m, 1H), 4.34 (m, 2H), 4.50 (m, 2H), 5.57 (d, 1H).

EXAMPLE 9

5-Acetamido-7-(6'-biotinylamino-caproyl-aminohexyl)-carbamoyl-4-guanidino-2,3,4,5-tetradeoxy-D-glycero-D-galacto-non-2-enopyranosonic acid (23)

This compound was prepared by coupling of biotinylaminocaproic acid and compound (18) using similar conditions to those described in Example 8.
$^1$H-nmr (CD$_3$OD) δ (ppm): 1.30–1.85 (m, 21H), 1.99 (s, 3H), 2.24 (m, 4H), 2.76 (d, 1H), 2.98 (dd, 1H), 3.05–3.3 (m, 7H), 3.50 (dd, 1H), 3.66 (m, 1H), 4.07 (m, 1H), 4.21 (m, 1H), 4.37 (m, 2H), 4.52 (m, 2H), 5.58 (d, 1H).

EXAMPLE 10

Preparation of 5-acetamido-7-(6'-(6"-(6"'-aminocaproyl-triaminocaproyl) -aminohexyl)-carbamoyloxy-4-guanidino-2,3,4,5-tetradeoxy-D-glycero-D-galacto-non-2-enopyranosonic acid (25)

(A) Preparation of methyl 5-acetamido-7-{6'-[6"-(6"'-tert-butoxycarbonylaminocaproyl)-tri-aminocaproyl]-aminohexyl}-carbamoyloxy-4-guanidino-8,9-monocarbonyldioxy-2,3,4,5-tetradeoxy-D-glycero-D-galacto-non-2-enopyranosonate (24).

To a solution of 6-[6'-(6"-tert-butoxycarbonyl-aminocaproyl)-di-aminocaproyl]-aminocaproic acid (150 mg, 0.263 mmol) in methanol (5 ml) at −20° C. were added successively potassium t-butoxide (30 mg, 0.267 mmol), N-methylmorpholine (15 mg, 0.148 mmol), and isobutyl chloroformate (40 mg, 0.293 mmol). The whole mixture was stirred under argon at −15~−20° C. for 20 min. before being combined with a solution of compound (18) (140 mg, 0.238 mmol) in a mixture of methanol (1.5 ml) and water (1.5 ml) containing triethylamine (38 mg, 0.372 mmol) at 0~5° C. The resulting reaction mixture was allowed to agitate at 15~20° C. for 4 hrs, then evaporated under reduced pressure to dryness. The residue was taken up in acetone (50 ml×2) and filtered to give a white solid (224 mg after air-drying) which was then chromatographed on silica gel (ethyl acetate/2-propanol/water=5/2/1) to afford compound (24) (80mg, 31.5%).
MS (FAB) 1068 (M+1)$^+$1067 (M$^+$)
$^1$H-nmr (CD$_3$D) d 1.21–1.72 (m, 41H), 1.99 (s, 3H), 2.18 (t, 8H), 2.92–3.24 (m, 12H), 3.79 (s, 3H), 4.14 (dd, 1H), 4.51–4.78 (m, 4H), 5.19 (ddd, 1H), 5.59 (dd, 1H) 5.92 (d, 1H).

(B) Preparation of compound (25)

Compound (24) (29.5 mg, 0.027 mmol) was dissolved in trifluoroacetic acid (2 ml) under argon. This mixture was stirred at room temperature for 1 hr, then evaporated under reduced pressure to dryness. The residue was redissolved in water (5 ml) and vacuum evaporated to dryness again before redissolving in water (2 ml) and freeze-drying to form a white solid. This solid was dissolved in a mixture of methanol (10 ml), water (10 ml) and triethylamine (5 ml). The resulting solution was allowed to agitate under argon at room temperature for 16 hr before being evaporated to dryness. It was redissolved in water (10 ml) and evaporated to dryness again. The residue was triturated successively in acetone (20 ml×3) and ethanol (20 ml), then freeze-dried to afford compound (25) (14 mg, 56%) as a white solid, which gave a positive Sakaguchi reaction and positive ninhydrin reaction.
MS (FAB) 927 (M+1)$^+$
$^1$H-nmr (D$_2$O) d 1.15–1.69 (m, 32H), 1.90 (s, 3H), 2.11–2.23 (m, 8H), 2.91–3.21 (m, 12H), 3.41–3.70 (m, 2H), 3.85–4.12 (m, 2H), 4.48–4.52 (m, 2H), 4.92 (dd, 1H), 5.58 (d, 1H).

EXAMPLE 11

Preparation of 5-acetamido-7-{6'-[6"-(6'''-biotinylaminocaproyl-triaminocaproyl]-aminohexyl}-carbamoyloxy-4-quanidino-2,3,4,5-tetradeoxy-D-glycero-D-galacto-non-2-enopyranosonic acid (26).

A solution of compound (24) (71.4 mg, 0.0667 mmol) in trifluoroacetic acid (2 ml) was stirred under argon at room temperature for 1 hr, then vacuum evaporated to dryness. The residue was dissolved in water (5 ml) and evaporated under reduced pressure to dryness. The resulting residue was dissolved in pyridine (6 ml) containing biotin-N-hydroxysuccinimde ester (36 mg, 0.105 mmol). The reaction mixture was stirred under argon at 40–50° C. for 48 hrs, then evaporated under reduced pressure to dryness. The resulting residue was stirred in acetone (30 ml) at room temperature for 4 hr and then filtered. The precipitate was washed with acetone (10 ml×2) and air-dried to afford a white solid (72 mg). This solid was stirred in a mixture of methanol (25 ml) and water (25 ml) containing triethylamine (5 ml) under argon at room temperature for 16 hrs before being vac-uum evaporated to dryness. The residue was subjected to chromatography (silica gel, the first run ethyl acetate/2-propanol/water=5/2/1 and the second run 2-propanol/water =3/1) to afford the title compound (26) (30.4 mg, 39.5%) as white solid, which gave a positive Sakaguchi reaction and a positive biotin colour reaction.
MS (FAB): 1153 (M+1)$^+$
infrared spectrum: 3292, 2931, 1638, 1541 cm$^{-1}$.
$^1$H-nmr (D$_2$O) d (ppm) 1.12–1.62 (m, 38H), 1.91 (s, 3H), 2.12 (m, 10H), 2.65 (d, 1H), 2.82–3.15 (m, 13H), 3.30–3.62 (m, 3H), 3.81–4.18 (m, 3H), 4.25–4.56 (m, 4H), 5.51 (d, 1H).

EXAMPLE 12

Preparation of 5-acetamido 7-{6'-[6"-(6'''-hydrazidosuccinylaminocaproyl)-triaminocaproyl]-aminohexyl}-carbamoyloxy-4-guanidino-2,3,4,5-tetradeoxy-D-glycero-galacto-non-2-enpyrnasonic acid (30)

To a solution of 6-(61-[61-(N-Boc-hydrazido succinyl)-aminocaproyl]-diaminocaproyl)-amino-caproic acid (100 mg, 0.146 mmol) in anhydrous methanol (4 ml) at –20° C. were successively added potassium tert-butoxide (16.4 mg, 0.146 mmol), N-methylmorpholine (14.7 mg, 0.146 mmol), and isobutyl chloroformate (24 mg, 0.176 mmol). The whole mixture was stirred at –15° C. for 12 min. before combining with a solution of 5-acetamido-7-(6'-aminohexyl)-carbamoyloxy-4-guanidino-2,3,4,5-tetradeoxy-D-glycero-D-galacto-non-2-enopyranosonic acid trifluoroacetic acid salt (11) (76.6 mg, 0.13 mmol) in a mixture of methanol (1.5 ml) and water (1.5 ml) containing triethylamine (16 mg, 0.158 mmol) at 5° C. The resulting reaction mixture was allowed to stir at room temperature for 2 hrs, then evaporated under reduced pressure to dryness. The residue was taken up in acetone (50 ml) and filtered. The solid wais washed with acetone (10 ml), then air-dried. It was subjected to column chromatography (silica gel, firstly ethyl acetate/2-propanol/water=5/2/1, then 2-propanol/water=3/1) to afford the compound (29) (63 mg 42.5%) as a white solid.
$^1$H-nmr (CD$_3$OD) δ (ppm)
1-21 ~1.72 (m, 41H), 1.95 (s, 3H), 2.17 (m, 8H), 2.48 (AB, 4H), 3.0~3.28 (m, 12H), 3.51 (dd, 1H), 3.62 (dd, 1H), 4.13 (m, 1H), 4.17 (dd, 1H), 4.35 (dd, 1H), 4.46 (dd, 1H), 4.98 (dd, 1H), 5.56 (d, 1H).

Compound (29) (60 mg, 0.0526 mmol) was stirred in trifluoroacetic acid (2 ml) under argon at room temperature for 1 hr, then vacuum evaporated to dryness. The residue was dissolved in water (5 ml) and evaporated under reduced pressure to dryness, then lyophilized to afford compound (34) tifluoroacetate as a white solid. This was dissolved in water (10 ml), treated with Amberlite IRA-400(OH—) resin to remove trifluoroacetic acid, and filtered off. The filtrate was evaporated to dryness. The residue was triturated in acetone (15 ml), then freeze-dried to afford the title compound (30) (40 mg, 73%) as a white solid which was stored under argon.
MS (FAB) 1041 (M+1)$^+$1042 (M+2)$^+$
$^1$H-nmr (D$_2$O) δ (ppm) (Trifluoroacetic acid salt)
1.15~1.68 (m,32H), 1.93 (8, 3H) 2.18 (m, 8H), 2.52 (AB, 4H), 2.98–3.23 (m, 12H), 3.40~4.20 (m, 4H), 4.42 (dd, 1H), 4.52 (dd, 1H), 4.92 (dd, 1H), 5.88 (d, 1H).

EXAMPLE 13

Preparation of methyl 5-acetamido-7-[6'-(3"-hydoxycarbonylpropionyl)-aminohexyl]-carbamoyloxy-4-guanidino-8,9-monocarbonyldioxy-2,3,4,5-tetradeoxy-D-glycerol-D-galacto-non-2-enopyranosonate (32)

To a solution of inethyl 5-acetamxido-7-(6'-aminohexyl)-carbamoyloxy-4-guanidino-8,9-monocarbonyldioxy-2,3,4,5-tetradeooy-D-glycero-D-galacto-non-2-enopyranosonate trifluoroacetate (18) (100 mg, 0.159 mol) in anhydrous pyridine (2.5 ml) were added dimethylaminopyridine (24 g, 0.195 mmol) and succinc anhydride (19.5 mg, 0.195 mmol). The miture was stirred under argon at 45° C. for 20 hrs then vacuum evaporated to remove pyridine. The residue was dissolved in methanol (10 ml) and acidified to pH 2 with 2N HCl, then the acidic solution was evaporated to dryness. The resulting residue was subjected to flash-chromatography (firstly ethyl acetate/methanol=10/1, then ethyl acetate/2-propanol/water=5/2/1, silica gel) to afford compound (32) (40 mg, 40%).
MS (FAB) 615 (M+1)$^+$
$^1$H-nmr (CD$_3$OD) δ (ppm)
1.25~1.62 (m, 8H), 1.93 (8, 3H), 2.48 (AB, 4H), 2.95~3.21 (m, 4H), 3.80 (s, 3H), 4.10~4.30 (m, 1H), 4.50~4.80 (m, 3H), 5.0–5.25 (m, 2H), 5.59 (dd, 1H), 5.92 (dd, 1H).

EXAMPLE 14

Determination of the binding of the compounds of the invention to influenza

Two influenza A virus strains and one influenza B virus were used to test the ability of the compounds to bind to whole virus influenza neuraminidase. The influenza A strains were NWS/G70C and NWS/Tokyo and the influenza B strain was B/Vic/02/87. The neuraminidase assay was carried out following a published procedure (Potier, M. et al, Anal. Biochem., 1979 29 287, and the measured inhibition constants ($IC_{50}$) are summarised in Table 3.

TABLE 3

Binding Constants (M) for Binding Influenza Viruses Compounds of the Invention

| Compound No. | NWS/Tokyo | NWS/G70C | B/Vic/02/87 |
|---|---|---|---|
| 8 | $4 \times 10^{-8}$ | $1 \times 10^{-8}$ | $7 \times 10^{-8}$ |
| 11 | $2 \times 10^{-8}$ | $2 \times 10^{-8}$ | not done |
| 13 | $2 \times 10^{-8}$ | $2 \times 10^{-8}$ | $8 \times 10^{-8}$ |
| 17 | $2 \times 10^{-8}$ | $2 \times 10^{-8}$ | $5 \times 10^{-7}$ |
| 19 | $1 \times 10^{-8}$ | $5 \times 10^{-9}$ | $2 \times 10^{-8}$ |
| 20 | $1 \times 10^{-5}$ | $1 \times 10^{-5}$ | not done |
| 21 | $4 \times 10^{-8}$ | $2 \times 10^{-8}$ | $1 \times 10^{-7}$ |
| 22 | $3 \times 10^{-8}$ | $5 \times 10^{-9}$ | $5 \times 10^{-8}$ |
| 23 | $2 \times 10^{-8}$ | $5 \times 10^{-9}$ | $6 \times 10^{-8}$ |
| 25 | $5 \times 10^{-8}$ | $4 \times 10^{-8}$ | $1 \times 10^{-7}$ |
| 26 | $2 \times 10^{-8}$ | $2 \times 10^{-8}$ | $4 \times 10^{-8}$ |
| DANA | $4 \times 10^{-5}$ | $1 \times 10^{-5}$ | $2 \times 10^{-5}$ |
| GG167(I) | $1 \times 10^{-8}$ | $1 \times 10^{-9}$ | $3 \times 10^{-9}$ |

EXAMPLE 15

Capture of Influenze Virus on to Avidin Coated ELISA Wells Using Compound No. 21

A 96 well ELISA plate was coated overnight with an acidin (Sigma) solution (10 μg/ml) . The plate wells were then blocked with a PBS (Phouphte buf fered saline)—Tween 20 solution. Compound No. 21 was added at 1 and 10 μm to all wells in each of two rows down the plate. Compound No. 8 (control) was added at 10 μM to all the wells in another row. After incubation for 1 hour at room temperature, unbound conjugate was removed and the plate was washed in PBS-Tween 20. NWS/G70C Influenza A virus (HIN9 subtype) was added, starting from $2.5 \times 10^6$ virus particles in the first well (equivalent to $5 \times 10^7$ pfu/ml), and diluting in serial two-fold dilutions across the plate. The virus was allowed to incubate for approximately 30 minutes and unbound virus was removed by washing. Bound virus was reacted with a polyclonal rabbit anti-hemagglutinin antibody and then the bound anti-hemagglutinin antibody was detected with a sheep anti-rabbit antibody-horseradish peroxidase (Ab-HRPO) conjugate, with washings at each step. Virus bound Ab-HRPO was detected by the addition of ABTS (Sigma) as the HRPO substrate and incubation for about thirty minutes.

Both concentrations (1 and 10 μM) of Compound Flo. 21 gave similar results; a strong absorption signal at the highest virus concentration and then a decreasing signal with virus dilution, thus clearly capturing virus and allowing detection down to at least $1.6 \times 10^5$ pfu per teat. In contrast, the non-biotinylated control Compound No. 8 showed only a weak, unchanging absorption at all virus concentrations.

EXAMPLE 16

Detection of Influenza Virus on ELISA Plates Using Compound No. 21

Starting with a virus solution of approximately $1 \times 10^8$ pfu/ml, serial two-fold dilutions of NWS/G70C influenza A virus in PBS were added directly on to an ELISA (Dynatech) plate and allowed to bind by standing overnight (all the ELISA wells contained 50 $\mu$l). After washing, the plates were blocked with PBS-Tween 20 and then Compound No. 21 was added at 1 and 10 $\mu$M to two separate rows, with control Compound No. 8 added at 10 $\mu$M to another row. After incubation for 1 hour the plates were washed to remove unbound compound and then the virus was detected with Streptavidin-HRPO (Boebringer-Mannheim), again using ABTS as the chromogenic substrate, with about thirty minutes incubation.

Both concentrations of Compound No. 21 allowed detection of the virus, giving an increasingly strong absorption in parallel with increasing virus concentration. A minimum of about $10^5$ virus particles per well could readily be detected with Compound No. 21. In contrast, this non-biotin control Compound No. 8 gave no signal at any concentration of virus.

EXAMPLE 17

Capture and detection of a complex between influenza and vorus and Compound No. 21

To allow coating ofvirus particles with the GG167-biotin derivative, 10, 2.5 and 0.625 $\mu$l of a solution of the NWS/G70C influenza A virus ($1\times10^8$ pfu/mxl) was pre-incubated for 1 hour in each well of separate rows of an ELISA plate. Half $\log_{10}$ dilutions of Compound No. 21 were added, starting from 1 $\mu$M and going down to 0.00001 $\mu$M. The virus-compound complexes were then transferred to an ELISA plate which had been pre-coated with avidin (as in Example 15) and incubated for 1 hour to allow capture. The plates were washed in PBS-Tween 20 and the captured virus was detected with a polyclonal rabbit antibody directed to the virus hemagglutinin (as in Example 15).

The best result was found with a 0.01 $\mu$M concentration of Compound No. 21, which clearly allowed detection of virus dow to $0.625\times10^5$ pfu. At higher concentrations of compound the signal was weaker, possibly due to the blocking of some avidin sites by free Compound No. 21, whilst at lower concentrations (<0.0001 $\mu$M) the detection signal was also weaker, probably due to there being insufficient compound to fully bind to all of the virus particles.

Direct detection of bound virus with streptavidin-HRPO was also found to be possible, though there was a lower level of signal in this case.

EXAMPLE 18

Capture and detection of a complex between influenza virus and Compound No. 26

Following the same procedure given in Example 17, but using the GG167-derivative Compound No. 26, it was found that the two subtypes of influenza A, NWS/G70C and NWS/Tokyo (H1N2), were both readily detected when present at $2.5\times10^5$ pfu/well. The concentrations of Compound No 26 tested were from 0.001 mM to 10 $\mu$M; the best results were obtained at 0.1 $\mu$M for both subtypes of virus.

It will be apparent to the person skilled in the art that while the invention has been described in some detail for the purpose of clarity and understanding, various modifications and alterations to the embodiments and methods described herein may be made without departing from the scope of the inventive concept disclosed in thiis specification.

The claims defining the invention are as follows:

1. A neuraminidase binder, in which the analogue of neuraminic acid is a compound of formula (II):

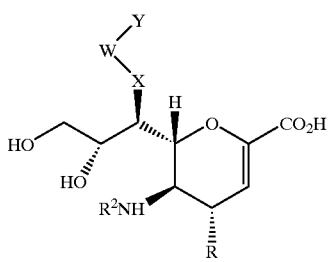
(II)

wherein
R represents an azido group, an unsubstituted or substituted guanidino group, or an unsubstituted or substituted amino group;
$R^2$ represents $COCH_3$, $COCF_3$ OR $SO_2CH_3$;
X represents O or NH;
W represents a spacer group made up of a chain of atoms having a total length of between four and one hundred atoms, and optionally also comprising substituted carbon and/or nitrogen atoms and optionally including oxygen and/or sulphur atoms;
Y represents OH, SH, $NH_2$, CH=O, $CH=CH_2$, $CO_2H$, $CONHNH_2$ OR NH-biotinyl, or a protected form of one of these end functionalities;
and wherein the substituent on the amino or guanidino group, when present, is a substituted or unsubstituted $C_{1-6}$ alkl group, or an amino, hydroxy, cyano or alkoxycarbonyl group;
with the proviso that X-W-Y does not include the group OC(=Z)$NR^5R^6$, wherein Z represents O or S, and $R^5$ and $R^6$ independently represents H or a hydrocarbon group optionally substituted by $NH_2$, OH or SH, but $R^5$ and $R^6$ are not both H.

2. A neuraminidase binder according to claim 1, in which the X-W-Y group attached at the 7-position is a terminally functionalized N

UNITED STATES PATENT AND TRADEMARK OFFICE
CERTIFICATE OF CORRECTION

PATENT NO. : 6,242,582 B1  Page 1 of 1
DATED : June 5, 2001
INVENTOR(S) : Phillip A. Reece et al.

It is certified that error appears in the above-identified patent and that said Letters Patent is hereby corrected as shown below:

Column 22,
Line 66, replace "in which the" with -- comprising an --,
Line 67, please delete "is a compound".

Signed and Sealed this

Twenty-sixth Day of August, 2003

JAMES E. ROGAN
*Director of the United States Patent and Trademark Office*